United States Patent
Nelson et al.

(10) Patent No.: US 10,745,333 B2
(45) Date of Patent: Aug. 18, 2020

(54) OPTIMIZATION OF O-SULFONATED PHENOL PRODUCTION FOR CUMENE HYDROPEROXIDE CLEAVAGE

(71) Applicant: SABIC GLOBAL TECHNOLOGIES B.V., Bergen op Zoom (NL)

(72) Inventors: Mark Erik Nelson, Mt. Vernon, IN (US); Arkady Samuilovich Dykman, St. Petersburg (RU); Andrey Vladimirovich Zinenkov, St. Petersburg (RU); Victor Vladimirovich Pinson, St. Petersburg (RU); Dmitrij Nikolayevich Zhukov, St. Petersburg (RU)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/268,042

(22) Filed: Feb. 5, 2019

(65) Prior Publication Data

US 2019/0177257 A1    Jun. 13, 2019

Related U.S. Application Data

(62) Division of application No. 15/501,186, filed as application No. PCT/IB2015/056024 on Aug. 7, 2015.

(30) Foreign Application Priority Data

Aug. 8, 2014 (RU) .................................. 2014132773

(51) Int. Cl.

| | |
|---|---|
| C07C 37/08 | (2006.01) |
| C07C 37/20 | (2006.01) |
| C07C 303/06 | (2006.01) |
| C07C 45/53 | (2006.01) |
| B01J 31/02 | (2006.01) |
| C07C 309/73 | (2006.01) |

(52) U.S. Cl.
CPC ........... *C07C 37/08* (2013.01); *B01J 31/0225* (2013.01); *C07C 37/20* (2013.01); *C07C 45/53* (2013.01); *C07C 303/06* (2013.01); *C07C 309/73* (2013.01); *Y02P 20/52* (2015.11)

(58) Field of Classification Search
None
See application file for complete search history.

(56) References Cited

U.S. PATENT DOCUMENTS

| | | | | |
|---|---|---|---|---|
| 5,733,340 | A * | 3/1998 | Lauton | C14C 3/28 8/94.33 |
| 6,943,270 | B2 | 9/2005 | Zakoshansky | |
| 7,482,493 | B2 | 1/2009 | Nelson et al. | |
| 7,485,758 | B2 | 2/2009 | Nelson et al. | |
| 8,030,525 | B2 | 10/2011 | Nelson et al. | |

FOREIGN PATENT DOCUMENTS

| | | |
|---|---|---|
| WO | 2008100165 A1 | 8/2008 |
| WO | 2009042246 A1 | 4/2009 |
| WO | 2010045423 A1 | 4/2010 |

OTHER PUBLICATIONS

Beyer Walter ed "Lehrbuch der Organische Chemie, Phenolsulfonsauren," Jan. 1, 1991, pp. 503, IBSN: 978-3-7776-0485-5.
International Search Report for International Application No. PCT/IB2015/056024; International Filing Date: Aug. 7, 2015; dated Nov. 16, 2015; 6 Pages.
Written Opinion for International Application No. PCT/IB2015/056024; International Filing Date: Aug. 7, 2015; dated Nov. 16, 2015; 8 Pages.

* cited by examiner

*Primary Examiner* — Samantha L Shterengarts
(74) *Attorney, Agent, or Firm* — Cantor Colburn LLP

(57) ABSTRACT

A method for the manufacture of a sulfonated phenol for use as a cumene hydroperoxide decomposition catalyst can comprise: combining phenol and a sulfonating agent at a first temperature that is 1° C. to 15° C. higher than a melting temperature of the phenol, to form a reaction mixture at the first temperature; reducing the first temperature of the reaction mixture to a second temperature that is 10 to 40° C. lower than the first temperature; and forming the sulfonated phenol at the second temperature.

10 Claims, No Drawings

OPTIMIZATION OF O-SULFONATED PHENOL PRODUCTION FOR CUMENE HYDROPEROXIDE CLEAVAGE

CROSS REFERENCE TO RELATED APPLICATIONS

This application is a divisional application of application Ser. No. 15/501,186, filed Feb. 2, 2017, which is a 371 of International Application No. PCT/IB2015/056024, filed Aug. 7, 2015, which claims priority to Russian Application No. 2014132773, filed Aug. 8, 2014, which are incorporated herein by reference in their entireties.

BACKGROUND

A method for the production of phenol and acetone can include the oxidation of cumene with atmospheric oxygen, followed by acid-catalyzed decomposition (also referred to as cleavage) of cumene hydroperoxide (CHP). In addition to CHP, the oxidation reaction can produce dimethylphenyl-carbinol (DMPC, also referred to as dimethylbenzyl alcohol (DMBA)). The decomposition reaction can be catalyzed with sulfuric acid and the process can be carried out in one or more stages.

A first stage can include decomposition of CHP and synthesis of dicumyl peroxide (DCP) from DMBA formed during oxidation. The second stage can include addition of an alkaline neutralization agent (e.g., ammonia) to quench excess sulfuric acid and reduce the acidity of the reacting mixture. The second stage can include decomposition of residual CHP, dehydration of residual DMBA and cleavage of DCP. This two-stage process can also result in the formation of byproducts, which can include hydroxyacetone (HA), α-methylstyrene (AMS), AMS dimers, acetophenone, cumyl phenols and heavy phenolic resins.

Hydroxyacetone can further react to form 2-methylbenzofuran, which can be difficult to separate from phenol and which can have an adverse effect on the color indexes of products made from impure commercial-grade phenol. Removal of hydroxyacetone from phenol can be performed, e.g., with the aid of alkaline or acidic treatments. However, such processes can be complicated, and can add reagents, process equipment, and controls, which can increase the cost of phenol production.

Accordingly, there exists a need in the production of phenol and acetone from cumene for a method to reduce the amount of byproducts in the phenol produced, reduce or eliminate entirely the addition of a alkaline neutralization agent, replace the neutralizing agent with a less costly agent, replace the neutralizing agent with a more readily available agent, increase the phenol and acetone yield or a combination comprising at least one of the foregoing.

BRIEF DESCRIPTION

A method for the manufacture of a sulfonated phenol for use as a cumene hydroperoxide decomposition catalyst can comprise: combining phenol and a sulfonating agent at a first temperature that is 1° C. to 15° C. higher than a melting temperature of the phenol, to form a reaction mixture at the first temperature; reducing the first temperature of the reaction mixture to a second temperature that is 10 to 40° C. lower than the first temperature; and forming the sulfonated phenol at the second temperature.

The above described and other features are exemplified by the following detailed description.

DETAILED DESCRIPTION

Decomposition of a $C_{8-12}$ alkylbenzene hydroperoxide to produce phenol and a $C_{3-6}$ ketone can be carried out in the presence of a protic acid catalyst, such as sulfuric acid. The acid catalyst can be mixed directly with a feedstock containing $C_{8-12}$ alkylbenzene hydroperoxide at a temperature of 40° C. to 75° C. in a reactor. The feedstock can be obtained from a $C_{8-12}$ alkylbenzene oxidation process and can include the $C_{8-12}$ alkylbenzene hydroperoxide, unreacted $C_{8-12}$ alkylbenzene, DMBA, acetophenone, or a combination including at least one of the foregoing. The reactor can include a recycle stream which can recirculate a portion of the reactor outlet stream to the reactor inlet. In this case, the catalyst concentration needed to achieve a desired product conversion can depend on the reaction mixture temperature, the ratio of phenol to $C_{3-6}$ ketone, the water content and the DMBA content in the feedstock.

The decomposition can be carried out in a multiple stage process. In an initial stage the feed rate of the feedstock can be maintained at a rate of less than or equal to 10% of the recycle rate, for example, less than or equal to 5%. In addition to the feedstock, the reactor can be provided a source of fresh $C_{8-12}$ alkylbenzene. The feed rate of fresh $C_{8-12}$ alkylbenzene can be maintained at a rate of less than or equal to 10% of the recycle rate, for example, less than or equal to 5%. Under the indicated conditions, a $C_{8-12}$ alkylbenzene hydroperoxide can decompose to form phenol and a $C_{3-6}$ ketone and can synthesize dialkyl benzyl peroxide from the $C_{8-12}$ alkylbenzene hydroperoxide and DMBA at a $C_{8-12}$ alkylbenzene hydroperoxide conversion rate of 95 to 99.9%. By products of the indicated conditions can include hydroxyacetone (HA), α-methylstyrene (AMS), AMS dimers, acetophenone, cumyl phenols or other components derived from other $C_{8-12}$ alkyl benzyl peroxides, or a combination including at least one of the foregoing. It has been found that the amount of AMS dimers, HA, and other byproducts can increase with increased protic acid concentration. Therefore, it can be important to control the amount of acid catalyst, provide an acid neutralizer, reduce the residence time of the reaction mixture, adjust the reaction temperature, adapt an alternative catalyst, or a combination including at least one of the foregoing strategies to limit the formation of undesired byproducts.

The synthesized dialkyl benzyl peroxide and the remaining $C_{8-12}$ alkylbenzene hydroperoxide can be decomposed in another stage at a temperature of 90° C. to 140° C. This stage can utilize an acid neutralizing agent to reduce the pH of the reaction mixture such that the temperature of the reaction mixture can be maintained. The pH of the reaction mixture can be controlled during the dialkyl benzyl peroxide reaction to convert the dialkyl benzyl peroxide and the remaining $C_{8-12}$ alkylbenzene to phenol and to a $C_{3-6}$ ketone while limiting the formation of undesired byproducts. One strategy for controlling the pH can be the addition of an acid suppressing agent. An acid suppressing agent can include an alkaline reagent, e.g., ammonia, carbonate, or the like. Another strategy for controlling the pH can include reducing the amount of acid used in the process thereby reducing and/or eliminating the need for an acid suppressing agent. One way to reduce the amount of acid can include the use of an ortho-sulfonated phenol catalyst in the alkylbenzene hydroperoxide decomposition phase, which can reduce the acidity of any recycle streams that are brought back to the alkylbenzene oxidation stage. Any of these strategies, or a combination of any of these strategies, can be used to control the pH value of the reaction mixture to 4 to 10, for example, 4.5 to 10, or 6.5 to 7.5.

The decomposition of a $C_{8-12}$ alkylbenzene hydroperoxide can be carried out in the presence of a sulfonated phenol catalyst. The sulfonated phenol catalyst can be prepared by combining a sulfonating agent and phenol to form a reaction mixture. The sulfonating agent and the phenol can be combined in a liquid phase. The reaction mixture can be combined at a combining temperature that is 1° C. to 15° C. greater than the melting point temperature of the phenol (e.g., pure phenol can have a melting point temperature of 40.8° C.). The addition of the sulfonating agent to the phenol can lower the melting point temperature of the reaction mixture below the melting point temperature of pure phenol. As a result, the temperature of the reaction mixture can be lowered to a forming temperature which can be 10° C. to 40° C. lower than the combining temperature without solidifying the reaction mixture. Furthermore, it has been found that the ratio of ortho-sulfonated phenol to para-sulfonated phenol can increase (e.g. a molar amount of ortho-substituted greater than or equal to the amount of para-substituted sulfonated phenol, 1:1 or greater portion of ortho-substituted phenol) as the formation temperature is reduced. The ortho-sulfonated phenol can provide higher activity to a $C_{8-12}$ alkylbenzene hydroperoxide decomposition reaction in comparison to para-sulfonated phenol. For example, when a $C_{8-12}$ alkylbenzene hydroperoxide is decomposed in the presence of an equal molar ratio (1:1) of ortho-sulfonated phenol to para-sulfonated phenol, the decomposition catalyst concentration can be approximately 50% the amount when compared to pure sulfuric acid (based on the mass of sulfuric acid used).

Additionally, providing an ortho-sulfonated phenol catalyst can reduce the formation of hydroxyacetone (HA) during decomposition in comparison to other methods (e.g., decomposition with a strong protic acid such as sulfuric acid, or with a catalyst having a higher ratio of para-sulfonated phenol or ortho-sulfonated phenol catalyst). For example, carrying out the $C_{8-12}$ alkylbenzene hydroperoxide decomposition reaction in the presence of the ortho-sulfonated phenol catalyst can reduce the amount of HA byproduct formed to less than or equal to 25% of the amount formed when the decomposition is carried out in the presence of the para-sulfonated phenol catalyst.

The sulfonated phenol catalyst can be formed at temperatures greater than or equal to 41.8° C., to avoid freezing of phenol, which can result in an ortho/para molar ratio (e.g., moles of ortho-sulfonated phenol divided by the moles of para-sulfonated phenol) of less than 0.5. In this case, the $C_{8-12}$ alkylbenzene hydroperoxide decomposition products can include greater than or equal to 700 parts per million by weight (ppmw) of hydroxyacetone (HA). However, when the $C_{8-12}$ alkylbenzene hydroperoxide decomposition reaction is carried out in the presence an ortho/para molar ratio of greater than or equal to 1 the concentration of HA in the decomposition product can be less than 1500 ppmw, for example, 600 ppmw to 1500 ppmw, or, 600 ppmw to 1000 ppmw, or, 600 ppmw to 800 ppmw.

While complete isolation of ortho-sulfonated phenol can be achieved, such procedure can rely on costly separation and/or purification processes. The cost to implement such separation and/or purification processes can increase the product cost. Therefore, a method of producing a larger molar amount of ortho-sulfonated phenol in comparison to para-sulfonated phenol while minimizing product cost impact can be desirable.

Combining the phenol and sulfonating agent reactants to form a reaction mixture can include heating, mixing (e.g., static and/or dynamic mixing) in a vessel, such as in a continually stirred tank reactor (CSTR), a plug-flow reactor, a batch reactor, or similar devices, and can further include adding, flowing, or otherwise introducing the sulfonating agent and the phenol to create the reaction mixture. The reaction mixture can be in the liquid phase, and can be maintained in the liquid phase throughout the production of the sulfonated phenol catalyst. A sulfonating agent can include sulfuric acid, acetyl sulfate, sulfur trioxide, fuming sulfuric acid (oleum), or a combination including at least one of the foregoing. The phenol can be molten, such as at a temperature above its melting point temperature. The reaction mixture can be maintained at a temperature above its melting temperature (e.g., temperature at which the reaction mixture starts to solidify when cooled, which can be less than the melting point temperature of pure phenol) while the sulfonation reaction is carried out. The reaction mixture can include phenol, a sulfonating agent, water, a $C_{8-12}$ alkylbenzene (e.g., cumene) sulfonation products, or a combination comprising at least one of the foregoing.

When sulfuric acid is used as the sulfonating reagent, reduced strength sulfuric acid can be used provided the reaction is sufficient. The initial mass ratio of phenol to sulfonating agent in the reaction mixture can be 1:2 to 1000:1, respectively. The reaction mixture can be maintained in a reactor at a temperature of 0° C. to 80° C., for example, 10° C. to 60° C., or 11.8° C. to 55.8° C., for a time period of 0.5 hours (hr) to 100 hr, for example, 1 hr to 20 hr, or, 3 hr to 8 hr.

The manufacture of ortho-sulfonated phenol catalyst can be carried out in a reactor having multiple zones. Each zone can be configured to impart a desired condition, e.g. pressure, temperature, phase, residence time, velocity, homogeneity, and the like. For example, in a zone of a reactor, the reactants can be combined to form a reaction mixture and heated (e.g., prior to being, during, or after being combined). In another zone of the reactor, the reactants and/or reaction mixture can be cooled to a desired temperature within a desired time period. In another zone of the reactor, the reaction mixture can be allowed to react to a desired extent of reaction. In an embodiment, a reactor can include three zones where the reactants are combined and/or heated in a first zone, cooled in a second zone, and the reaction is allowed to proceed at a cooler temperature in the third zone. In a further embodiment of a three zone reactor, the second zone can have a smaller volume than the third zone and can impart a residence time of 0.01 hr to 0.2 hr to the reaction mixture.

The ortho-sulfonated phenol can be used in a $C_{8-12}$ alkylbenzene hydroperoxide decomposition process to form phenol, a $C_{3-6}$ ketone, a $C_{2-6}$ alkylaldehyde, or a combination including at least one of the foregoing. The $C_{8-12}$ alkylbenzene hydroperoxide decomposition process can include multiple stages. A stage of the $C_{8-12}$ alkylbenzene hydroperoxide decomposition process can include mixing the ortho-sulfonated phenol catalyst, acetone, water, $C_{8-12}$ alkylbenzene hydroperoxide in a reaction vessel at a reaction temperature. The reaction temperature can be 40° C. to 90° C., for example, 40° C. to 70° C. Cleaving the $C_{8-12}$ alkylbenzene hydroperoxide at these temperatures can allow for reducing the amount of protic acid catalyst in comparison to other cleaving methods. As a result, the process can be carried out without the use of an acid neutralizing agent (e.g., such as ammonia, acetone, water, and the like). For example, additional stages can be free of a feed of an acid neutralizing agent as the amount of acid used in the first stage can be reduced.

Under these process conditions, the amount of $C_{8-12}$ alkylbenzene hydroperoxide exiting a first reaction stage can be maintained equal to or lower than 1.0 wt. %. Additionally, the amount of hydroxyacetone exiting a final stage can be controlled at less than 700 ppmw, for example, 500 ppmw to 400 ppmw, or 300 ppmw, which can significantly affect the quality of the commercial phenol product produced by the process. Moreover, the reduction in the amount of sulfuric acid can lead to a reduction in the consumption of alkali used to neutralize the acid, which ultimately reduces the amount of mineral wastes, such as sodium sulfate, of the production process.

A $C_{8-12}$ alkylbenzene can include any $C_{8-12}$ alkylbenzene, for example, isopropylbenzene (cumene), sec-butylbenzene, diisopropylbenzene, or a combination including at least one of the foregoing. A $C_{3-6}$ ketone can include any $C_{3-6}$ ketone, for example, acetone, methyl ethyl ketone (MEK or butanone), pentanone, hexanone, cyclohexanone, or a combination including at least one of the foregoing.

Decomposing a $C_{8-12}$ alkylbenzene hydroperoxide in the presence of an o-sulfonated phenol as discussed herein can reduce the amount of byproducts present in the phenol produced, reduce or eliminate entirely the addition of a alkaline neutralization agent, replace the neutralizing agent with a less costly agent, replace the neutralizing agent with a more readily available agent, increase the phenol and acetone yield, or a combination comprising at least one of the foregoing

EXAMPLES

Hydroperoxide cleavage was carried out using a test installation including a 12 ml glass reactor with circulation loop equipped with a circulation pump (up to 1000 milliliter per hour (ml/hr) flow rate), a hydroperoxide feed inlet, and a catalyst inlet, and with static mixers built in the circulation loop to provide a uniformly mixed circulation stream. The reactor temperature was controlled by passing heat transfer liquid through the reactor jacket. A portion of the reaction mixture from the circulation loop was passed through an intermediate vessel and was pumped through a second plug flow cleavage reactor of 10 milliliter (ml) volume equipped with an electric heater to provide the desired reaction temperature.

The cleavage catalyst prepared in situ by feeding phenol and sulfonating agent through the temperature-controlled tee mixer having an after-mixing volume of 0.4 microliter (μl) (e.g., hot part of catalyst preparation reactor) and passing the resulting mixture through a capillary PTFE tube (cold part of catalyst preparation reactor) placed inside temperature-controlled enclosure and tailing end attached to the circulation loop inlet of cleavage reactor.

The alkylbenzene hydroperoxide feed was prepared by oxidation of hydrocarbon and included side products of the oxidation reaction as is shown in the following tables.

Example 1

A cumene hydroperoxide stream of the composition presented in Table 1 was fed at a rate of 25 grams per hour (g/h) into the above described cleavage test reactor. Cleavage catalyst was prepared by simultaneously pumping 0.7 microliter per hour (μl/h) of 96 wt. % sulfuric acid and 2.4 μl/h of phenol into the tee mixer at 50° C., and passing the resulting mixture through the 305 millimeter (mm) long capillary tube of 0.5 mm inside diameter (ID), having 60 μl volume and providing a 20 hour residence time at 20° C. The reaction product compositions are presented in Table 2.

TABLE 1

Feed Composition

| Component | Content, wt. % |
|---|---|
| Cumene hydroperoxide (CHP) | 82.55 |
| Cumene | 11.88 |
| Dimethylbenzyl alcohol (DMBA) | 3.97 |
| Acetophenone | 0.61 |
| Water | 0.06 |
| Dicumylperoxide (DCP) | 0.62 |
| Phenol | 0.02 |
| Not identified | 0.29 |
| Total | 100 |

TABLE 2

Reaction Mixture Composition

| Component | Composition, wt. % |
|---|---|
| Phenol | 40.75 |
| Acetone | 44.56 |
| Dicumylperoxide (DCP) | 0.14 |
| Dimethylbenzyl alcohol (DMBA) | 0.07 |
| Culylphenols | 0.18 |
| α-Methylstyrene dimers (DAMS) | 0.12 |
| Acetophenone (AP) | 0.51 |
| α-Methylstyrene (AMS) | 2.58 |
| Cumene | 9.69 |
| Hydroxyacetone (HA) | 0.04 |
| Mesityl oxide | 0.01 |
| Not identified | 0.46 |
| Water | 0.89 |
| Total | 100 |

Example 2

The cleavage process was carried out in the same manner as is presented in Example 1, but the catalyst was prepared by feeding 0.5 μl/h of 20% fuming sulfuric acid (oleum) and 5.5 μl/h phenol into the mixing tee at 56° C., and passing the resulting mixture through the 40 mm long capillary tube reactor of 0.31 mm ID at 46° C. providing a 0.5 hour residence time. The reaction product compositions are presented in Table 3.

TABLE 3

Reaction Mixture Composition

| Component | Composition, wt. % |
|---|---|
| Phenol | 40.61 |
| Acetone | 44.79 |
| Dicumylperoxide (DCP) | 0.15 |
| Dimethylbenzyl alcohol (DMBA) | 0.08 |
| Culylphenols | 0.16 |
| α-Methylstyrene dimers (DAMS) | 0.11 |
| Acetophenone (AP) | 0.51 |
| α-Methylstyrene (AMS) | 2.50 |
| Cumene | 9.59 |
| Hydroxyacetone (HA) | 0.04 |

TABLE 3-continued

Reaction Mixture Composition

| Component | Composition, wt. % |
|---|---|
| Mesityl oxide | 0.01 |
| Not identified | 0.49 |
| Water | 0.93 |
| Total | 100 |

Example 3

The cleavage process was carried out in the same manner as is presented in Example 1, but the catalyst was prepared by feeding 0.6 μl/h of 96 wt. % sulfuric acid and 1.8 μl/h phenol into the mixing tee at 45° C., and passing the resulting mixture through the 480 mm long capillary tube reactor of 0.8 mm ID at 5° C. providing a 100 hour residence time. The reaction product compositions are presented in Table 4.

TABLE 4

Reaction Mixture Composition

| Component | Composition, wt. % |
|---|---|
| Phenol | 40.86 |
| Acetone | 44.55 |
| Dicumylperoxide (DCP) | 0.11 |
| Dimethylbenzyl alcohol (DMBA) | 0.06 |
| Culylphenols | 0.18 |
| α-Methylstyrene dimers (DAMS) | 0.13 |
| Acetophenone (AP) | 0.54 |
| α-Methylstyrene (AMS) | 2.44 |
| Cumene | 9.63 |
| Hydroxyacetone (HA) | 0.03 |
| Mesityl oxide | 0.01 |
| Not identified | 0.52 |
| Water | 0.94 |
| Total | 100 |

Example 4

The cleavage process was carried out in the same manner as is presented in Example 1, but with a feed composition as is presented in Table 5. The catalyst was prepared by feeding 0.7 μl/h of 96 wt. % sulfuric acid and 2.4 l/h phenol into the mixing tee at 50° C., and passing the resulting mixture through the 305 mm long capillary tube reactor of 0.5 mm ID at 20° C. providing a 20 hour residence time. The reaction product compositions are presented in Table 6.

TABLE 5

Hydroperoxide Mixture Cleavage Feed

| Component | Content, wt. % |
|---|---|
| Cumene hydroperoxide (CHP) | 67.35 |
| sec-Butylbenzene hydroperoxide | 17.76 |
| Cumene | 1.27 |
| sec-Butylbenzene | 8.61 |
| Dimethylbenzyl alcohol (DMBA) | 3.19 |
| Acetophenone | 0.74 |

TABLE 5-continued

Hydroperoxide Mixture Cleavage Feed

| Component | Content, wt. % |
|---|---|
| Water | 0.06 |
| Dicumylperoxide (DCP) | 0.42 |
| Phenol | 0.01 |
| Not identified | 0.59 |
| Total | 100 |

TABLE 6

Reaction mixture composition

| Component | Composition, wt. % |
|---|---|
| Phenol | 41.25 |
| Acetone | 40.05 |
| Methylethylketone (MEK) | 6.20 |
| Dicumylperoxide (DCP) | 0.11 |
| Dimethylbenzyl alcohol (DMBA) | 0.06 |
| Culylphenols | 0.13 |
| α-Methylstyrene dimers (DAMS) | 0.08 |
| Acetophenone (AP) | 0.61 |
| α-Methylstyrene (AMS) | 1.99 |
| Cumene | 1.02 |
| sec-Butylbenzene | 6.94 |
| Hydroxyacetone (HA) | 0.03 |
| Not identified | 0.80 |
| Water | 0.73 |
| Total | 100 |

Example 5

The cleavage process was carried out in the same manner as is presented in Example 1, but with a feed composition as is presented in Table 7. The catalyst was prepared by feeding 0.8 μl/h of 96 wt. % sulfuric acid and 2.4 μl/h phenol into the mixing tee at 42° C., and passing the resulting mixture through the 47 mm long capillary tube reactor of 0.5 mm ID at the same temperature providing a 3 hour residence time. The reaction product compositions are presented in Table 8.

TABLE 7

Cumene Hydroperoxide Cleavage Feed

| Component | Content, wt. % |
|---|---|
| Cumene hydroperoxide (CHP) | 82.15 |
| Cumene | 12.02 |
| Dimethylbenzyl alcohol (DMBA) | 4.06 |
| Acetophenone | 0.67 |
| Water | 0.11 |
| Dicumylperoxide (DCP) | 0.64 |
| Phenol | 0.02 |
| Not identified | 0.33 |
| Total | 100 |

TABLE 8

Reaction Mixture Composition

| Component | Composition, wt. % |
|---|---|
| Phenol | 40.75 |
| Acetone | 44.62 |
| Dicumylperoxide (DCP) | 0.08 |

TABLE 8-continued

| Reaction Mixture Composition | |
|---|---|
| Component | Composition, wt. % |
| Dimethylbenzyl alcohol (DMBA) | 0.07 |
| Culylphenols | 0.19 |
| α-Methylstyrene dimers (DAMS) | 0.13 |
| Acetophenone (AP) | 0.51 |
| α-Methylstyrene (AMS) | 2.57 |
| Cumene | 9.67 |
| Hydroxyacetone (HA) | 0.05 |
| Mesityl oxide | 0.01 |
| Not identified | 0.46 |
| Water | 0.89 |
| Total | 100 |

Embodiment 1: A method for the manufacture of a sulfonated phenol for use as a cumene hydroperoxide decomposition catalyst, comprising: combining phenol and a sulfonating agent at a first temperature that is 1° C. to 15° C. higher than a melting temperature of the phenol, to form a reaction mixture at the first temperature; reducing the first temperature of the reaction mixture to a second temperature that is 10 to 40° C. lower than the first temperature; and forming the sulfonated phenol at the second temperature.

Embodiment 2: The method of Embodiment 1, wherein the phenol and the sulfonating agent are combined in a molar ratio of 50:1 to 1:3.

Embodiment 3: The method of any of Embodiments 1-2, wherein the phenol and the sulfonating agent are combined in a molar ratio of 4:1 to 1:1.

Embodiment 4: The method of any of Embodiments 1-3, wherein the sulfonating agent comprises sulfuric acid, acetyl sulfate, sulfur trioxide, fuming sulfuric acid, or a combination comprising at least one of the foregoing.

Embodiment 5: The method of any of Embodiments 1-4, wherein the combining comprises adding the sulfonating agent to the phenol.

Embodiment 6: The method of any of Embodiments 1-5, comprising forming o-sulfonated phenol and p-sulfonated phenol in a weight ratio of o-sulfonated phenol to p-sulfonated phenol greater than or equal to 1.

Embodiment 7: The method of any of Embodiments 1-6, further comprising maintaining the second temperature over a time period of 0.5 hours to 100 hours.

Embodiment 8: The method of any of Embodiments 1-6, further comprising maintaining the second temperature over a time period of 1 hour to 20 hours.

Embodiment 9: The method of any of Embodiments 1-6, further comprising maintaining the second temperature over a time period of 3 hours to 8 hours.

Embodiment 10: The method of any of Embodiments 1-9, wherein the combining is in a first reactor zone, the reducing the first temperature is in a second reactor zone, and the forming is in a third reactor zone.

Embodiment 11: The method of Embodiment 10, where the second reactor zone is smaller in volume than the third reactor zone and imparts a residence time of approximately 0.01-0.2 hours, and wherein the residence time is less than or equal to 1% of a total reaction time.

Embodiment 12: The method of any of Embodiments 1-11, wherein the method is conducted in a plug-flow reactor.

Embodiment 13: A sulfonated phenol formed by the method of any of Embodiments 1-12.

Embodiment 14: A method for the cleavage of a $C_{8-12}$ alkylbenzene hydroperoxide into phenol and a $C_{3-6}$ ketone, comprising; contacting the $C_{8-12}$ alkylbenzene hydroperoxide with a catalytically sufficient amount of the sulfonated phenol of any of Embodiments 1-12 under conditions effective to cleave the $C_{8-12}$ alkylbenzene hydroperoxide to form the phenol, the $C_{3-6}$ ketone, a $C_{2-6}$ alkylaldehyde, or a combination comprising at least one of the foregoing.

Embodiment 15: The method of Embodiment 14, wherein the catalytically sufficient amount is 10-500 ppm by weight.

Embodiment 16: The method of Embodiment 14, wherein the catalytically sufficient amount is 10-80 ppm by weight.

Embodiment 17: The method of any of Embodiments 14-16, further comprising diluting the sulfonated phenol with the corresponding $C_{8-12}$ alkyl benzene of the $C_{8-12}$ alkylbenzene hydroperoxide before the contacting.

Embodiment 18: The method of Embodiment 14, further comprising maintaining a concentration of hydroxyacetone of less than or equal to 900 parts per million by weight.

Embodiment 19: The method of Embodiment 14, further comprising maintaining a concentration of hydroxyacetone of less than or equal to 700 ppmw.

Embodiment 20: The method of Embodiment 14, further comprising maintaining a concentration of hydroxyacetone of less than or equal to 500 ppmw.

Embodiment 21: The method of Embodiment 14, further comprising maintaining a concentration of hydroxyacetone of less than or equal to 400 ppmw.

Embodiment 22: The method of Embodiment 14, further comprising maintaining a concentration of hydroxyacetone of less than or equal to 300 ppmw.

Embodiment 23: The method of any of Embodiments 14-22, wherein the $C_{8-12}$alkylbenzene comprises cumene, and the $C_{3-6}$ ketone comprises acetone.

Embodiment 24: The method of any of Embodiments 14-22, wherein the $C_{8-12}$ alkylbenzene comprises ethyl benzene, and the alkylaldehyde comprises acetaldehyde.

Embodiment 25: The method of any of Embodiments 14-22, wherein the $C_{8-12}$ alkylbenzene comprises sec-butyl benzene, and the $C_{3-6}$ ketone is methyl ethyl ketone.

Embodiment 26: The method of any of Embodiments 14-22, wherein the $C_{8-12}$ alkyl benzene is cyclohexyl benzene and the $C_{3-6}$ ketone is cyclohexanone.

Embodiment 27: Phenol and a $C_{3-6}$ ketone formed by the method of any of Embodiments 14-26.

Embodiment 28: Phenol and acetone formed by the method of any of Embodiments 14-26.

Embodiment 29: A method for the manufacture of bisphenol A, comprising contacting the phenol of Embodiment 28, the acetone of Embodiment 28, or both under conditions effective to form bisphenol A.

Embodiment 30: Bisphenol A formed by the method of Embodiment 29.

Embodiment 31: A method for the manufacture of a polycarbonate, comprising contacting the bisphenol A of Embodiment 29 with a carbonyl source under conditions effective to form the polycarbonate.

Embodiment 32: A polycarbonate formed by the method of Embodiment 31.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents. I/we claim:

The invention claimed is:

1. A method for the manufacture of a sulfonated phenol for use as a cumene hydroperoxide decomposition catalyst, comprising:

combining phenol and a sulfonating agent at a first temperature that is 1° C. to 15° C. higher than a melting temperature of the phenol, to form a reaction mixture at the first temperature;

reducing the first temperature of the reaction mixture to a second temperature that is 10 to 40° C. lower than the first temperature; and forming the sulfonated phenol at the second temperature.

2. The method of claim 1, wherein the phenol and the sulfonating agent are combined in a molar ratio of 50:1 to 1:3.

3. The method of claim 1, wherein the sulfonating agent comprises sulfuric acid, acetyl sulfate, sulfur trioxide, fuming sulfuric acid, or a combination comprising at least one of the foregoing.

4. The method of claim 1, wherein the combining comprises adding the sulfonating agent to the phenol.

5. The method of claim 1, comprising forming o-sulfonated phenol and p-sulfonated phenol in a weight ratio of o-sulfonated phenol to p-sulfonated phenol greater than or equal to 1.

6. The method of claim 1, further comprising maintaining the second temperature over a time period of 0.5 hours to 100 hours.

7. The method of claim 1, wherein the combining is in a first reactor zone, the reducing the first temperature is in a second reactor zone, and the forming is in a third reactor zone.

8. The method of claim 7, where the second reactor zone is smaller in volume than the third reactor zone and imparts a residence time of approximately 0.01-0.2 hours, and wherein the residence time is less than or equal to 1% of a total reaction time.

9. The method of claim 1, wherein the method is conducted in a plug-flow reactor.

10. A sulfonated phenol formed by the method of claim 1, comprising o-sulfonated phenol and p-sulfonated phenol in a weight ratio of o-sulfonated phenol to p-sulfonated phenol greater than or equal to 1.

* * * * *